(12) United States Patent
Jackson, III

(10) Patent No.: US 10,828,071 B2
(45) Date of Patent: Nov. 10, 2020

(54) HINGED ANTERIOR CERVICAL LOCKING PLATE SYSTEM

(71) Applicant: Avery M. Jackson, III, Grand Blanc, MI (US)

(72) Inventor: Avery M. Jackson, III, Grand Blanc, MI (US)

(73) Assignee: Avery M. Jackson, Grand Blanc, MI (US)

( * ) Notice: Subject to any disclaimer, the term of this patent is extended or adjusted under 35 U.S.C. 154(b) by 145 days.

(21) Appl. No.: 15/438,603

(22) Filed: Feb. 21, 2017

(65) Prior Publication Data
US 2018/0235671 A1     Aug. 23, 2018

(51) Int. Cl.
*A61B 17/70*     (2006.01)
*A61B 17/80*     (2006.01)

(52) U.S. Cl.
CPC ...... *A61B 17/7059* (2013.01); *A61B 17/8023* (2013.01); *A61B 17/8057* (2013.01)

(58) Field of Classification Search
CPC ............ A61B 17/8023; A61B 17/8042; A61B 17/8033; A61B 17/7059; Y10T 16/5367; Y10T 16/554; Y10T 16/53613
See application file for complete search history.

(56) References Cited

U.S. PATENT DOCUMENTS

| | | |
|---|---|---|
| D376,971 S | 12/1996 | Schutz |
| 5,843,082 A | 12/1998 | Yuan et al. |
| 6,602,256 B1* | 8/2003 | Hayes ................ A61B 17/7059 606/296 |
| 6,645,208 B2 | 11/2003 | Apfelbaum et al. |
| 6,878,167 B2* | 4/2005 | Ferree .................... A61B 17/15 623/17.16 |
| 7,547,306 B2 | 6/2009 | Michelson |
| 8,172,191 B1* | 5/2012 | Zimbalatti ............. F16M 11/10 16/266 |
| 8,262,710 B2 | 9/2012 | Freedman et al. |
| 10,363,072 B2 | 7/2019 | Bauerle et al. |

(Continued)

OTHER PUBLICATIONS

Notification of Transmittal of the International Search Report and the Written Opinion of the International Searching Authority, or the Declaration for corresponding International Application No. PCT/US17/28457; filed Apr. 19, 2017.

*Primary Examiner* — Amy R Sipp
(74) *Attorney, Agent, or Firm* — McNees Wallace & Nurick LLC

(57) ABSTRACT

A folding anterior cervical locking plate system for stabilizing the cervical spine in a spinal fusion procedure. The plate system has at least two plate sections hinged together by a hinge structure at adjacent ends for pivoting movement of the plate sections relative to one another through at least 90° in each of two directions. A first hole in each plate section enables visualization of the underlying graft. A locking plate spans adjacent ends of the plate sections and holes in the locking plate are aligned with holes in adjacent plate sections so pedicle screws inserted through the holes in the locking plates extend through the holes in the plate sections to secure the system to the vertebral bodies and stabilizes the cervical spine. In one embodiment the locking plate slides in guide channels on opposite side edges of the plate sections.

20 Claims, 6 Drawing Sheets

(56) References Cited

U.S. PATENT DOCUMENTS

| | | | |
|---|---|---|---|
| 2002/0151896 A1* | 10/2002 | Ferree | A61B 17/7059 |
| | | | 606/279 |
| 2003/0229348 A1* | 12/2003 | Sevrain | A61B 17/7059 |
| | | | 606/70 |
| 2006/0089648 A1 | 4/2006 | Masini | |
| 2006/0271052 A1* | 11/2006 | Stern | A61B 17/7059 |
| | | | 606/71 |
| 2006/0276794 A1* | 12/2006 | Stern | A61B 17/7059 |
| | | | 606/71 |
| 2007/0293865 A1 | 12/2007 | Ko | |
| 2008/0161861 A1* | 7/2008 | Huebner | A61B 17/8033 |
| | | | 606/286 |
| 2008/0195158 A1* | 8/2008 | De Villiers | A61B 17/7059 |
| | | | 606/280 |
| 2008/0244866 A1 | 10/2008 | Stanley | |
| 2009/0043341 A1 | 2/2009 | Tyber et al. | |
| 2009/0163960 A1* | 6/2009 | Binder | A61B 17/1728 |
| | | | 606/280 |
| 2009/0326589 A1 | 12/2009 | Lemoine et al. | |
| 2013/0060288 A1* | 3/2013 | Rodgers | A61B 17/1604 |
| | | | 606/281 |
| 2013/0173004 A1* | 7/2013 | Greenhalgh | A61F 2/4455 |
| | | | 623/17.16 |
| 2013/0310650 A1* | 11/2013 | Hales | A61B 1/267 |
| | | | 600/188 |
| 2015/0173812 A1 | 6/2015 | Masson | |
| 2015/0366595 A1* | 12/2015 | Kaufmann | A61B 17/8052 |
| | | | 606/290 |
| 2016/0000482 A1* | 1/2016 | Ehmke | A61B 17/8009 |
| | | | 606/71 |
| 2016/0066969 A1 | 3/2016 | Reuter | |
| 2019/0388126 A1* | 12/2019 | Sheffer | A61B 17/7067 |
| 2020/0015863 A1* | 1/2020 | Ganter | A61B 17/7065 |

* cited by examiner

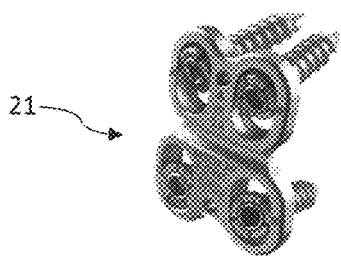
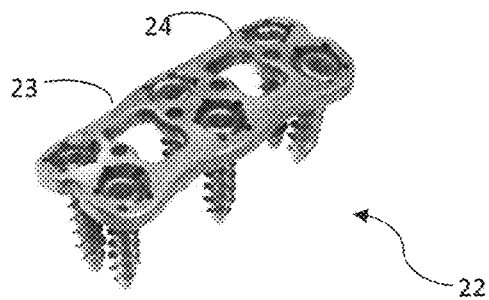
FIG. 6 (PRIOR ART)  FIG. 7 (PRIOR ART)
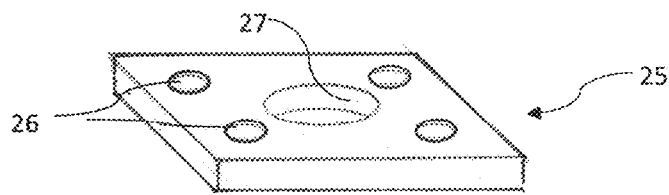
FIG. 8 (PRIOR ART)
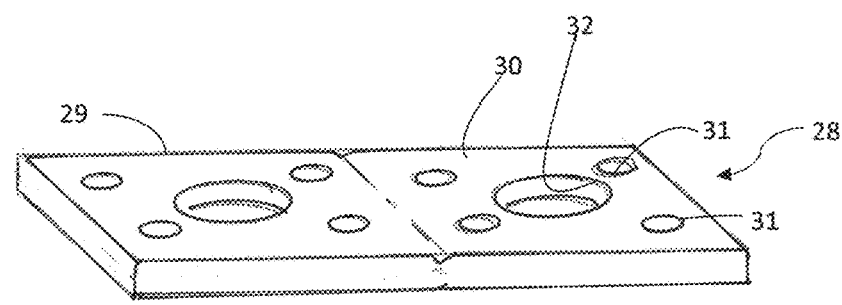
FIG. 9 (PRIOR ART)
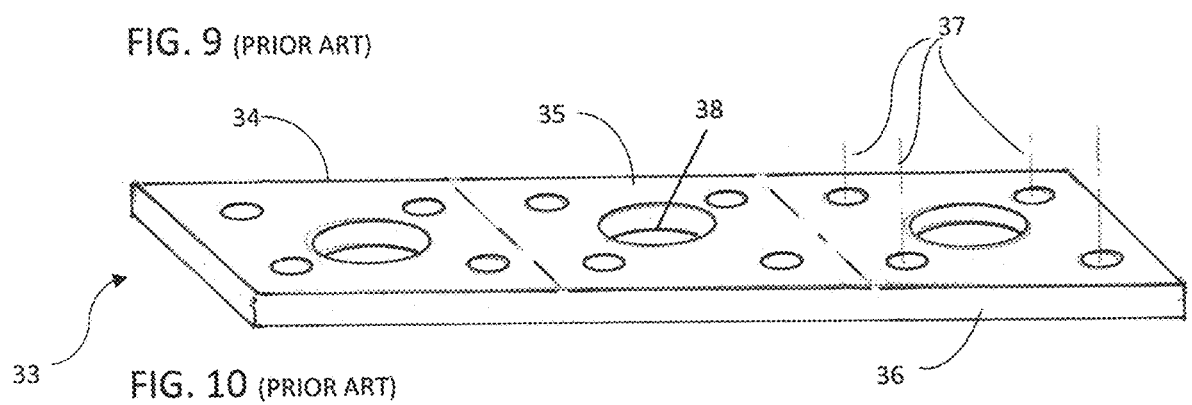
FIG. 10 (PRIOR ART)

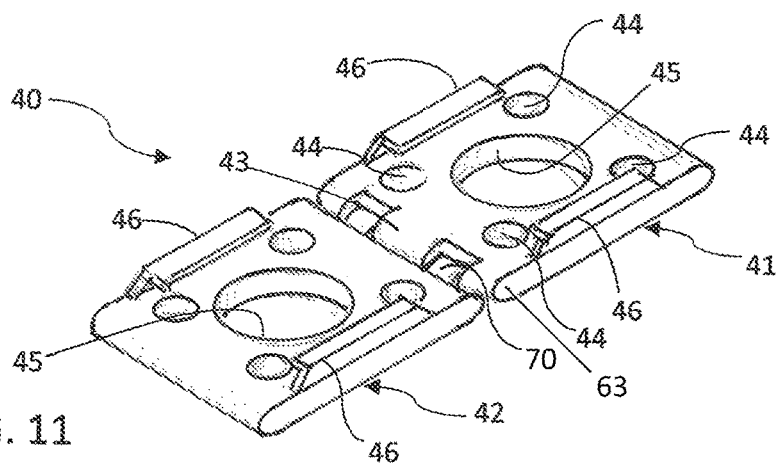
FIG. 11
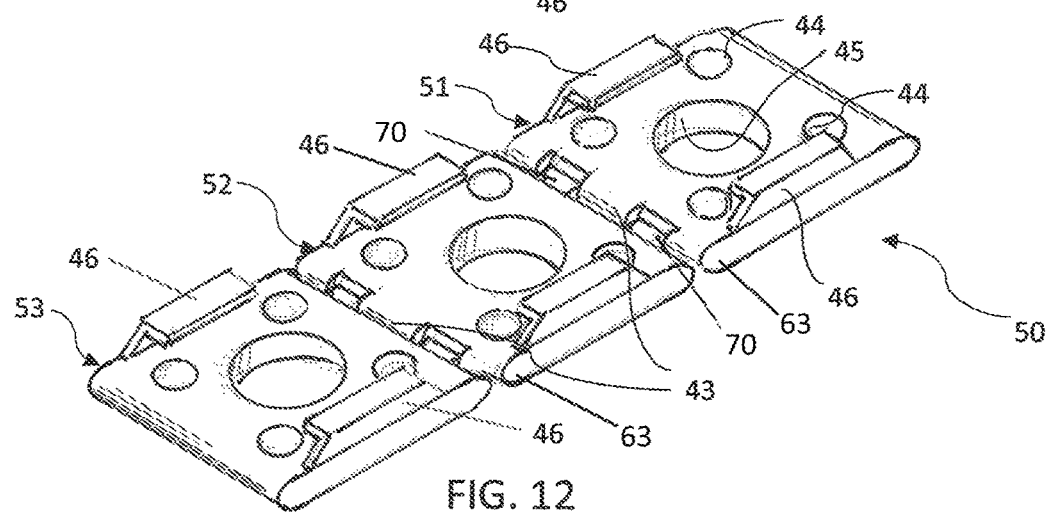
FIG. 12
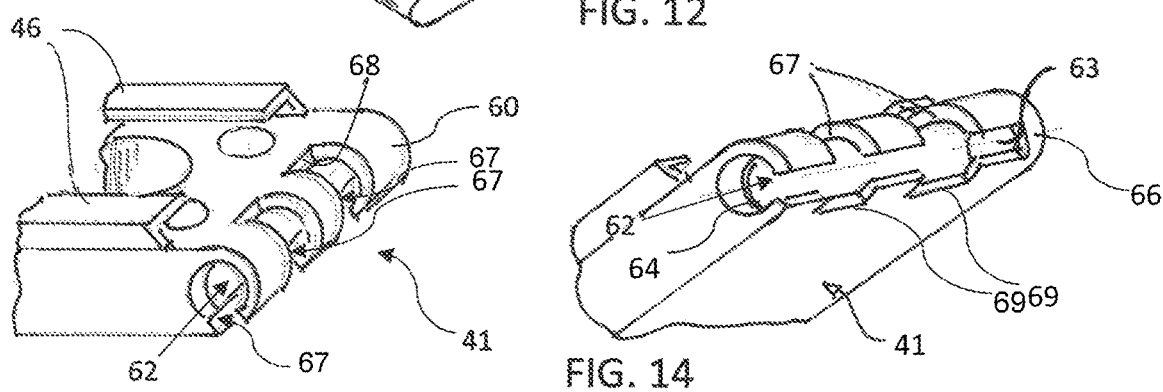
FIG. 13
FIG. 14
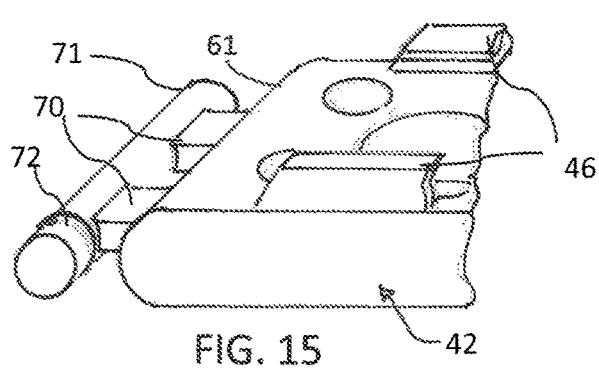
FIG. 15

HINGED ANTERIOR CERVICAL LOCKING PLATE SYSTEM

TECHNICAL FIELD

This invention relates to an implantable plate system for fixation at the anterior face of the vertebral bodies of the cervical spine to stabilize adjacent cervical vertebrae as an adjunct to treatment of spinal disorders. More particularly, the locking plate system of the invention has hinged together sections that can be folded relative to one another to facilitate placement in the area being treated and unfolded in place to span the desired levels. Different numbers of plats can be quickly and easily connected together or disconnected when desired to change the number of levels the plate system spans.

BACKGROUND ART

The cervical spine comprises seven cervical vertebrae named by their position in order from C1 adjacent the skull to C7 adjacent the thoracic spine. The C1 vertebra supports the skull and is named the atlas. The C2 vertebra is named the axis and provides the axis upon which the skull and atlas rotate when the head is moved side to side. Intervertebral discs are located between adjacent vertebra except the first two cervical vertebrae, C1 and C2. Motion between adjacent vertebrae occurs through the disc and two facet joints.

As people age the discs lose some of their water content and consequently some of their shock absorbing ability. Tears may form without symptoms in the outer ring or annulus of the disc and heal by forming scar tissue. Scar tissue is weaker than normal tissue, and as the disc continues to wear it begins to collapse and the space between adjacent vertebrae becomes smaller, affecting alignment of the facet joints in the back of the spine. The change in the way the bones fit together causes abnormal pressure on the articular cartilage, and over time this abnormal pressure causes wear and tear arthritis (osteoarthritis) of the facet joints.

Other disorders include spinal disc herniation, fractured or dislocated vertebrae, spinal stenosis, and cervical spondylotic myelopathy. Most neck pain is due to degenerative changes. Perhaps the most serious of the problems caused by degeneration of the spinal segments in the cervical spine is the condition of spinal stenosis, which typically occurs during the later stages of spinal degeneration. In the cervical spine this condition is sometimes called cervical myelopathy.

In cervical spinal stenosis, the spinal canal narrows and can squeeze and compress the nerve roots where they leave the spinal cord, or the spinal cord itself may be compressed. Spinal stenosis is most common in people older than age 50. The aging process can cause a bulging of the discs or a thickening of tissues that connect bones. These disorders can result in nerve compression, leading to paralysis, numbness, or pain.

The vast majority of patients who have neck pain will not require any type of operation. However, in some cases degenerative changes in the cervical spine can lead to a very serious condition where there is too much pressure on the spinal cord. When this condition occurs, the entire spinal cord is in danger.

One surgical option is to remove the pressure on the spinal cord by removing the offending disc or discs, called a discectomy, and to place a bone graft in the space left by removal of the disc. A fusion surgery is almost always done at the same time as the discectomy in order to stabilize the cervical segments. Together, the combined surgery is commonly referred to as an ACDF surgery, which stands for Anterior Cervical Discectomy and Fusion. It may be done for one level or for more than one level of the cervical spine. While this surgery is most commonly done to treat a symptomatic cervical herniated disc, it may also be done for other cervical degenerative diseases.

In the case of a degenerative vertebra, the degenerative vertebra or vertebrae are removed and replaced with a bone graft to fill the space left by removal of the degenerative vertebra. This procedure is called a corpectomy and strut graft. Any bone spurs pushing on the spinal cord are also removed during a corpectomy procedure. A corpectomy is often performed in association with some form of discectomy. In either case, the graft heals over time to create a spinal fusion where the disc or vertebral body has been removed.

Although the cervical spine can be approached from either the front (anterior approach) or from the back (posterior approach), the discs are more directly accessible from the front of the neck and if conditions permit, most surgeons favor an anterior approach. An anterior approach results in less disruption of the normal musculature and it is also easier to maintain the normal alignment of the spine. Many degenerative conditions of the spine cause a loss of the normal lordosis (gentle curvature of the spine). By opening up the front of the spine in an anterior approach, this lordosis can be reestablished.

The anterior approach provides better access to the spine because almost the entire cervical spine is accessible. It provides access to the spine through a relatively uncomplicated pathway, and there generally is less postoperative pain. In a discectomy, the discs can be reached without disturbing the spinal cord, spinal nerves, and neck muscles. All things being equal, the patient tends to have less incisional pain from this approach than from a posterior operation. Depending on the particular symptoms, one disc (single-level) or multiple discs (multi-level) may be removed.

In performing anterior fusion surgery on the cervical spine, a cut is made either transversely or longitudinally in the front of the patient's neck, depending upon the surgeon's training and the levels of surgical fusion. A transverse incision can be made when a one or two level fusion is to be made. When more than a two level fusion is to be made, a longitudinal incision is generally required. The incision length depends on the size of the person and the number of levels to be treated.

In accordance with one procedure for anterior access to the cervical spine, a transverse incision 2-4 centimeters long, depending on the size of the patient and the number of levels, is made just off the midline in the front of the neck, and the cervical fascia is gently divided in a natural plane, between the esophagus and carotid sheath. Small retractors and an operating microscope are used to allow the surgeon to visualize the anterior vertebral body and discs. The arteries and nerves in the neck are protected while the muscles and other tissues are moved to the side.

After the spinal cord and nerve roots have been decompressed at the appropriate levels, the portions removed must be reconstructed so as to support the normal loads of the cervical spine by inserting either a bone graft within each disc space, or inserting a longer graft, referred to as a strut graft, to span the space left by removing one or more vertebral bodies. The intent is to promote the formation of a living bridge of bone between the vertebrae above and below the space formed by removal of one or more vertebrae. The patient's own bone or human cadaver bone may be used to form the graft, or a synthetic scaffold may be used into which bone graft is inserted.

Plating systems have been developed in the prior art to fixedly connect two or more vertebrae to each other and stabilize the cervical spine while the fusion heals. These plating systems typically comprise plates made of titanium and designed to be secured with screws to the vertebrae above and below the fusion. A plate spans the gap between two adjacent vertebrae, and the screws go through holes in the plate and into the vertebrae. Each vertebra may receive one screw or two or more screws depending on the type of plate which is utilized.

The plate system can span one level, i.e. the space between two adjacent vertebrae, or two levels, i.e. the spaces between three adjacent vertebrae, or more levels depending upon the requirements for treating a particular disorder. Once the fusion bone and cervical plate are in place, the vertebrae are stabilized and the bony fusion occurs according to biological healing principles.

Conventional plates are either pre-assembled by the manufacturer into multiple level options, or the plate is assembled by the surgical scrub technicians on the back table then handed to the surgeon for insertion. Plates are usually provided in sets having a range of sizes so as to provide for such features as biological diversity in size, the numbers of segments to be joined, and the length of the portions of bone to be joined. Plating systems are typically designed for joining from two to five vertebrae.

To place the cervical plates, the tissue in front of the vertebrae must be moved to one side to expose the vertebrae. This involves moving the larynx, the pharynx, the esophagus, carotid artery, several important nerves, and dissecting several muscles. Swallowing issues can arise after surgery, particularly when multiple levels are involved, due to the trauma caused when placing a long rigid plate in a small opening with anatomic structures in close proximity Forcing a large plate for a multi-level fusion into a smaller opening could lead to a dysfunction in esophageal motility, which can affect the swallowing mechanism and the voice.

After gaining access to the prevertebral space and performing the discectomy and fusion, an anterior plate sized to span the number of levels involved, e.g. connecting two motion two vertebrae or one motion segment, is selected. The plate is then placed with fingers or forceps onto the anterior vertebral body surface and screws are inserted through the plate and into the vertebrae to secure the plate to the vertebrae.

It can be extremely difficult to safely place longer multi-level plates into the resection bed because it is difficult to safely retract the soft tissues that must be moved out of the way to place the longer plate for multilevel constructs. There is a potential for resultant esophageal tear or stretch injuries and a risk of causing dysphagia, especially with retraction of the cephalad oropharyngeal tissues when placing the plate. The plate is usually larger than the surgical dissection and requires extra retraction or soft tissue manipulation. Traversing venous or arterial structures are also at risk when placing longer plates. Swallowing dysfunction of some degree is likely. A hoarse voice from injury to the laryngeal nerve or superior thyroid nerve may occur during plate placement and manipulation.

One known complication arising from anterior cervical fusion with conventional plating systems is injury to the esophagus. The risk goes up as the dimensions of the plate increase. Injury to the esophagus can result during surgery when a large, rigid prior art plating system is forced into position through the surgical wound, leading to erosion through the esophagus.

Accordingly, there is need for a plate system that in multi-level fusion surgery avoids the need to force a large plate through the small surgical opening and past surrounding tissue.

SUMMARY OF THE INVENTION

The present invention is a folding plate system that avoids the need to force a large plate into the smaller soft tissue space when multi-level anterior fusion is being performed. The plating system of the invention allows the surgeon to avoid soft tissue injury leading to swallowing dysfunction or vascular injury. The plate system is folded to its folded configuration and in this form inserted through the incision and positioned at the anterior surface of the cervical spine. It is then gently lengthened by flattening the plate completely from its folded position into its unfolded final position. This maneuver is performed while the plate system is sitting on the anterior surface of the cervical vertebrae. The surgeon does not have to wrestle with multi-level plates by stretching soft tissues for plate placement. Holes in the plates provide visualization of the end plates of the underlying vertebral bodies where the disc spaces are located.

The multi-link plate system of the invention removes the risk of esophageal injury because the plate is not forced into the surgical wound. Instead, it is placed in segments in a modular fashion or an accordion fashion and then expanded after it is positioned at the front of the spine below the esophagus and other soft tissues.

The plate system of the invention comprises two or more plate sections that each span a single level. A single plate section could be used for one level and multiple plate sections hinged together for multiple levels. Thus, two plate sections are hinged together for two levels, three plate sections are hinged together for three levels, and so on. The hinged-together plate sections can be folded relative to one another to reduce the length of the system for easier insertion into the space being operated on, especially in multi-level fusion surgery.

A locking plate is extended across the hinged connection between two adjacent plate sections to lock the plate sections against movement after they are unfolded and secured in place on the bony anatomy.

The plate sections are able to be folded enough relative to one another (120° in either direction in a specific example) so that the system of hinged together plate sections is significantly shorter in length when folded than a conventional one-piece multi-level plate. After insertion, the folded plate sections can be unfolded internally to place them in position on the spine. They can be folded up again internally if the plate system needs to be removed for some reason, e.g. exchanged for another plate system.

In a preferred example, each plate section measures 2-3 mm in thickness, 6-10 mm in width, and 20-30 mm in length. The overall length of a plate system would depend upon the number of levels involved. The locking plates preferably are 1-2 mm thick and each one is sized to overlap the joint between adjacent plate sections. In a preferred embodiment, the plate sections and locking plate are made of titanium, but in an alternate embodiment they can be 3-D printed.

In one embodiment, guide channels are on opposite side edges of the top of the plate sections and the locking plate is slidably guided at its opposite edges in these channels so that it can be moved from an unlocked position to a locked position in spanning relationship across the hinge between adjacent plate sections. Holes in the locking plate can line up with holes in the plate sections so that screws inserted through the holes secure the locking plate and the plate sections in position.

In another embodiment, the guide channels are omitted and the locking plate is added after the plate sections are in position. No sliding mechanism is required. In this configuration, the screws that hold the locking plate in position across the hinge also hold the plate sections to the vertebral body.

BRIEF DESCRIPTION OF THE DRAWINGS

The foregoing as well as other objects and advantages of the invention will become apparent from the following detailed description when considered in conjunction with the accompanying drawings, wherein like reference characters designate like parts throughout the several views, and wherein:

FIG. 6 is an isometric view of a prior art plate for single level fusion.

FIG. 7 is an isometric view of a prior art plate for two level fusion.

FIG. 8 is a schematic isometric representation of a prior art plate for single level fusion.

FIG. 9 is a schematic isometric representation of a prior art plate for two level fusion.

FIG. 10 is a schematic isometric representation of a prior art plate for three level fusion.

FIG. 11 is an isometric view of a first form of plate system according to the invention, wherein two plate sections are hinged together for use in a two level fusion.

FIG. 12 is an isometric view of the first form of plate system, wherein three plate sections are hinged together for use in a three level fusion.

FIG. 13 is an enlarged, fragmentary, top isometric view of one end of one of the plate sections in the first form of the invention.

FIG. 14 is an enlarged, fragmentary, bottom isometric view of the end shown in FIG. 13.

FIG. 15 is a top isometric view of the opposite end of the plate section shown in FIGS. 11-14.

DETAILED DESCRIPTION OF THE PREFERRED EMBODIMENTS

Figure 1:
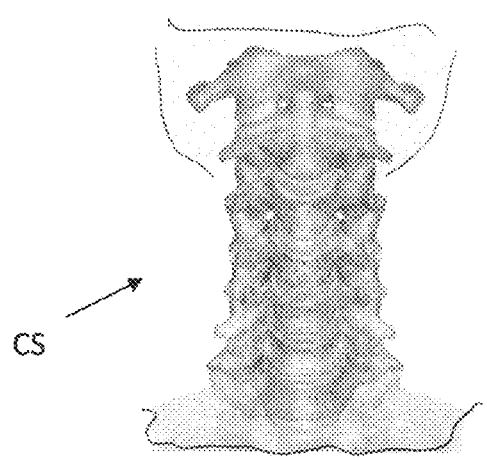
FIG. 1 is a schematic front representation of the cervical spine.
Figure 2:
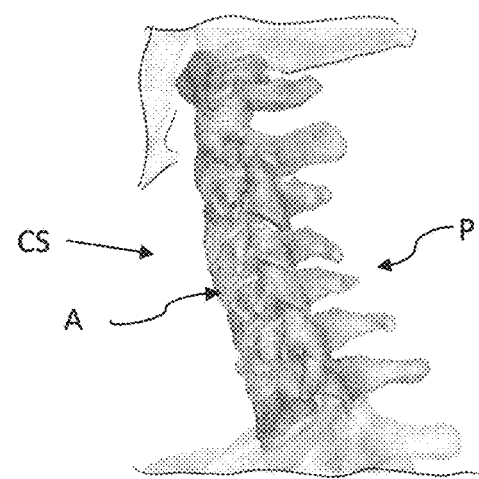
FIG. 2 is a schematic side representation of the cervical spine.

A representative front view of a cervical spine CS is shown in FIG. 1, and the anterior surface A and posterior surface P are indicated in the side view of FIG. 2.

Figure 3:
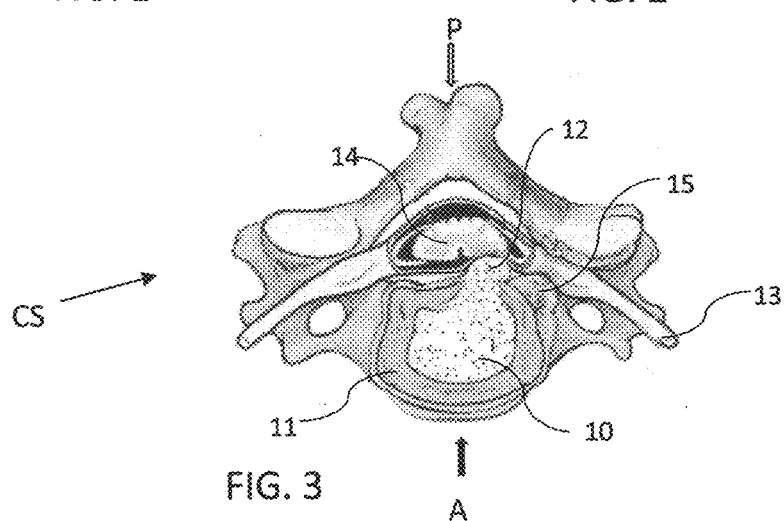
FIG. 3 is a schematic cross sectional view of the cervical spine, showing a typical bone spur and herniated disc.

A cross section of the cervical spine CS is shown in FIG. 3. The section is taken through a disc 10 and its associated annulus 11, with the annulus shown ruptured and a herniation 12 of the disc compressing a nerve 13 leading from the spinal cord 14. A bone spur 15 is also shown compressing the nerve 13.

Figure 4:
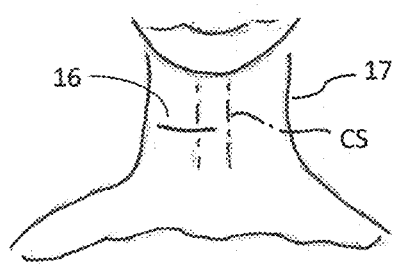
FIG. 4 is a fragmentary schematic front view of a patient's neck, showing a typical transverse incision made in an anterior fusion surgery procedure.

A transverse incision 16, offset slightly to one side of the cervical spine, is made in the front of a patient's neck 17 in FIG. 4. It should be understood that depending upon the requirements of a particular procedure, the incision can be made either transversely, as shown, or longitudinally.

Figure 5:
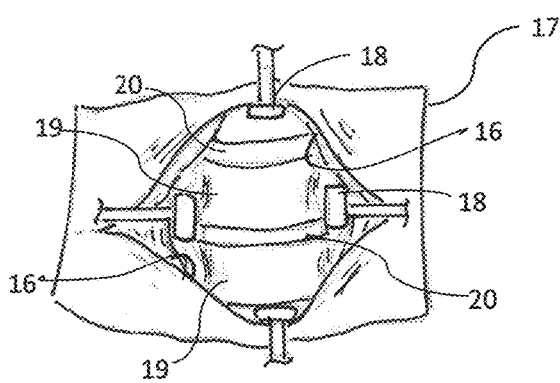
FIG. 5 is an enlarged fragmentary schematic front view of a patient's neck after retractors have been used to open the incision and move adjacent tissue aside to gain access to the cervical spine.
Figure 16:
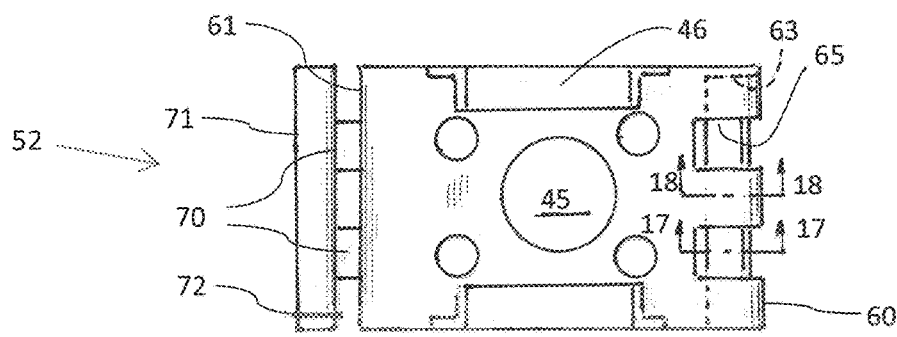
FIG. 16 is a top plan view of one of the plate sections in FIGS. 11-14.
Figure 17:
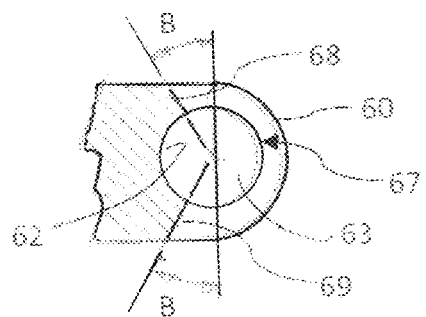
FIG. 17 is an enlarged fragmentary sectional view taken along line 17-17 in FIG. 16.

Retractors 18 are being used in FIG. 5 to spread open the incision and hold other tissue to the side to expose the vertebrae 19 and discs 20 at the anterior surface of the cervical spine.

FIGS. 6-10 depict prior art devices. A prior art plate for single level fusion is shown at 21 in FIG. 6, and a prior art plate for two level fusion is shown at 22 in FIG. 7. The two level plate 22 is a single unitary piece with portions 23 and 24 adapted to be positioned over adjacent discs, for example.

FIG. 8 is a schematic illustration of a prior art plate 25 for single level fusion. In this particular example, the plate has four holes 26 for receiving screws to fasten the plate to vertebral bodies and a single large hole 27 to enable visualization of the graft site and end plates.

FIG. 9 is a schematic illustration of a prior plate 28 for two level fusion. This plate is of one-piece construction and comprises two sections 29 and 30 adapted to overlie respective fusion sites. Each has holes 31 for receiving screws to fasten the plate to vertebral bodies, and a large centrally located hole 32 to enable visualization of the graft sites and end plates.

A prior art plate 33 for three level fusion is shown in FIG. 10. This plate is also of one-piece construction and has three sections 34, 35 and 36 adapted to overlie respective fusion sites. In this particular example, each section has four holes for receiving screws at 37 to fasten the plate to vertebral bodies, and a large centrally located hole 38 to enable visualization of the graft sites and end plates.

A two level plate system according to a first form of the invention is indicated generally at 40 in FIG. 11. This plate system comprises two plate sections 41 and 42 hinged together at 43 at adjacent ends for pivoting movement through at least 90° in each direction, and preferably through 120°. Each plate section has four holes 44 in the specific example shown for receiving screws to fasten the plate system to vertebral bodies. A large central hole 45 is provided to enable visualization of the graft sites and end plates. Guide channels 46 extend along opposite side edges of each plate section on the upper surface thereof to receive and guide a locking plate as described hereinafter.

A three level plate system according to the first form of the invention is indicated generally at 50 in FIG. 12. This plate system comprises three plate sections 51, 52 and 53 hinged together at 43 at adjacent ends. Each plate section has four holes 44 in the specific example shown for receiving screws to fasten the plate system to vertebral bodies, and a large central hole 45 to enable visualization of the graft sites and end plates. Guide channels 46 extend along opposite side edges of each plate section on the upper surface thereof to receive and guide a locking plate as described hereinafter. Additional levels can be added, depending upon the requirements of a particular procedure. Cervical fusion surgery can involve up to seven levels.

It should be understood that a different number of holes 44 could be provided in the forms of invention described above, but four holes are typical and are illustrated and described in the specific examples disclosed herein.

In the forms of the invention shown in FIGS. 11 and 12, the manufacturer could supply sets of two, three, four, or more plate sections hinged together and the surgeon would select an appropriate set, depending upon the number of levels involved. In an alternate embodiment, some or all of the plate sections could have hinge-forming structures at both ends and the surgeon or surgical assistant could assemble as many plate sections as necessary for a particular procedure.

Details of the hinged ends are shown in FIGS. 13-19. Referring first to FIGS. 11, 13, 14, 17 and 18, the ends 60 and 61 of plate sections 41 and 42 are rounded and a cylindrical bore 62 (see FIGS. 13 and 14) extends transversely through end 60 of plate section 41 from one side of the plate section to the opposite side, which is optionally closed at 63 (see FIGS. 14 and 16). An annular groove 64 is formed in the wall of the bore near the open end (see FIGS. 14 and 20).

Figure 18:
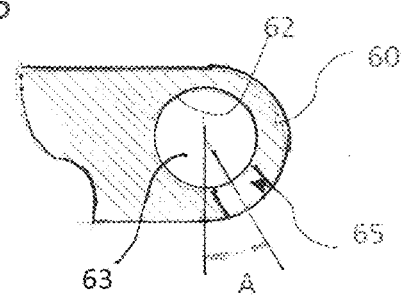
FIG. 18 is an enlarged fragmentary sectional view taken along line 18-18 in FIG. 16.

A slot 65 is formed in a lower portion of the rounded end 60, spaced counterclockwise at an angle A of about 30° from a vertical plane drawn through the longitudinal centerline of the bore 62 (see FIGS. 14 and 18). The slot opens into the bore 62 over most of the width of the plate section 41 except for a short section 66 where the slot terminates short of the closed end of the bore.

Notches 67 are formed in the rounded end 60 transversely to the slot 65 and intersect the slot at two spaced apart locations along the length of the bore 62. The notches terminate at their upper end 68 in the top of the plate section and at their lower end 69 in the bottom of the plate section, the terminal ends being spaced rearwardly at an angle B of about 30° from a vertical plane drawn through the longitudinal centerline of the bore 62 (see FIG. 17).

As seen best in FIGS. 15, 16, 19 and 20, a pair of support arms 70 extend from the rounded end 61 of plate section 42, supporting a cylindrically shaped hinge pin 71 in spaced relation to the end 61. An annular bead 72 on the outer surface of pin 71 near one end engages in groove 64 to restrain pin 71 against axial movement in the bore 62 when the pin is fully inserted into the bore. The closed end 63 of the bore limits insertion of the pin into the bore so that the bead 72 engages in the groove 64 when the parts are assembled into operative position.

Figure 19:
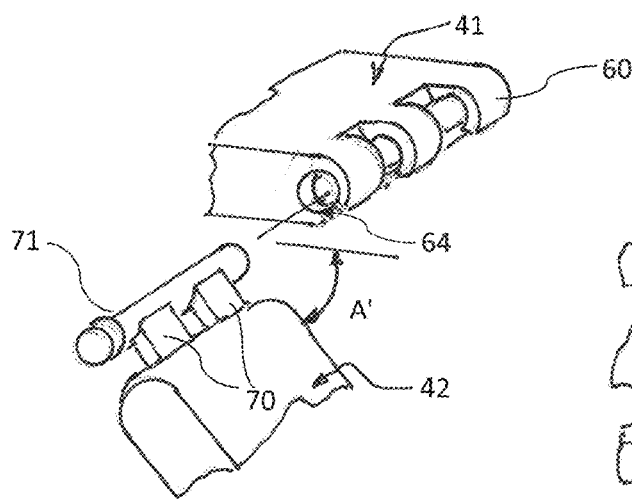
FIG. 19 is an exploded, fragmentary, top isometric view showing how two plate sections are oriented so that they can be assembled at the hinged ends.
Figure 20:
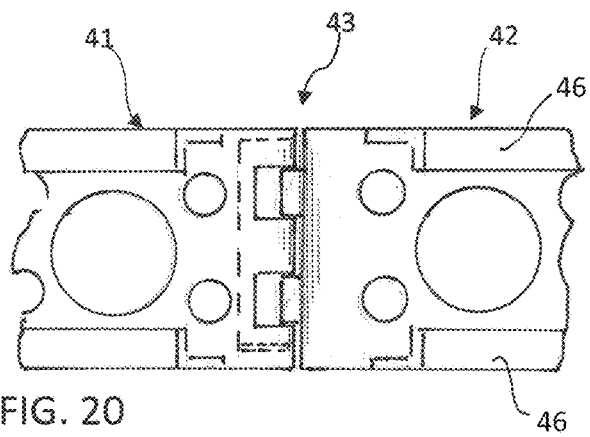
FIG. 20 is a fragmentary top plan view showing two plate sections assembled together at the hinged ends.

To assemble the plate sections 41 and 42 or 51, 52 and 53 together, or other multiples of plate sections (not shown), the plate sections are angled relative to one another as shown in FIG. 19 so that plate section 42, for example, is at an angle A' of 60° below the plane of plate section 41. The pin is inserted endwise into the bore 62 until one of the support arms 70 engages the closed end 66 of slot 65 (see FIG. 14), and/or, if provided, the end of the pin 71 abuts against closed end 63 of bore 62. This lines up the support arms 70 with notches 67 so that the plates 41 and 42 can be pivoted 120° in either direction (see FIG. 21). This also lines up the bead 72 with groove 64 which when engaged form a detent to prevent relative axial movement between pin 71 and bore 62 and prevent the two plate sections from unintentionally disconnecting from one another but permitting it when sufficient force is exerted.

Figure 21:
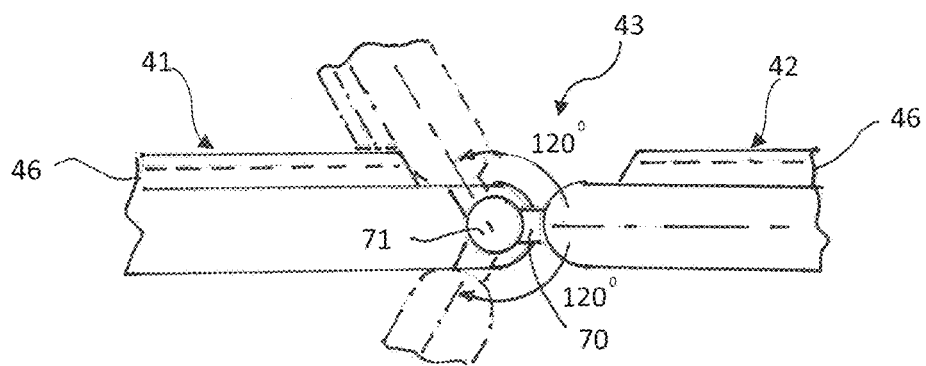
FIG. 21 is an enlarged fragmentary view in elevation of two plate sections hinged together and illustrating the range of pivoting movement between them.
Figure 22:
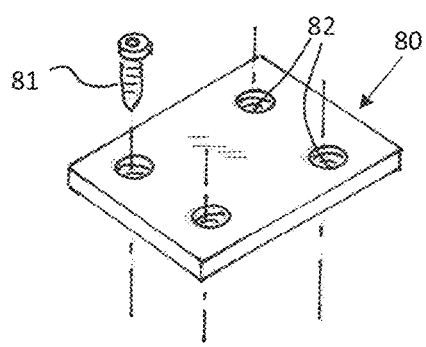
FIG. 22 is an exploded top isometric view of one of the screws and a locking plate that spans the hinged connection between two hinged together plate sections.

As noted above, when connected the plate sections can pivot 120° in either direction relative to one another as shown in FIG. 21. This facilitates insertion of the plate system into position on the cervical spine without having to force it into surrounding tissue. When the plate system is in position on the anterior surface of the cervical vertebrae it is secured in place with screws passed through the holes 44 as explained hereinafter.

Figure 23:
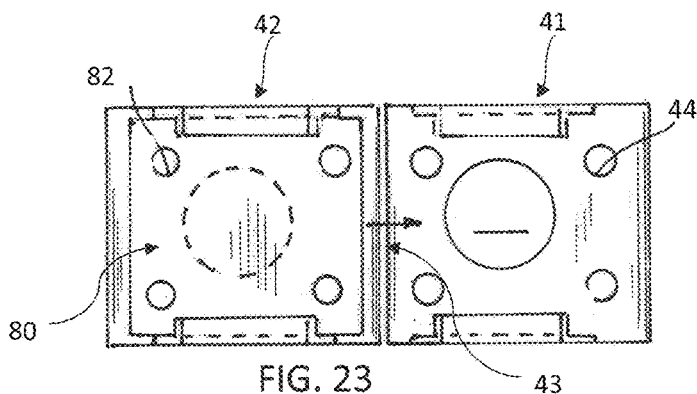
FIG. 23 is a top plan view of two hinged together plate sections and a locking plate slidably engaged at its opposite side edges in the channels on one of the plate sections prior to the locking plate being moved across the hinged connection between the two plate sections.
Figure 24:
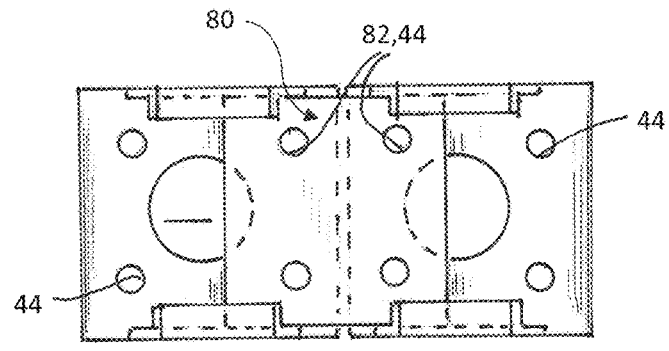
FIG. 24 is a top plan view showing the locking plate of FIG. 23 moved into operative position across the hinged connection between the two plate sections.
Figure 25:
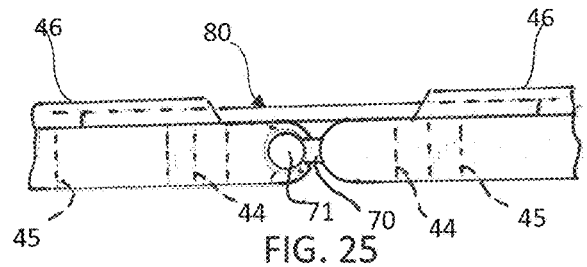
FIG. 25 is a fragmentary side view in elevation of the plate sections and locking plate of FIG. 24.

To lock the pivotally connected plate sections in their operative unfolded position and stabilize the spine to which they are attached, a locking plate 80 spans each hinged area 43. The locking plate is secured with screws 81 extended through openings 82 in the locking plate 80 and through the openings 44 in the plate sections 41 and 42 and then into the underlying vertebrae. In this regard, the holes 82 are located so that they line up with the holes 44 when the locking plate is in the positions shown in FIGS. 23 and 24.

In that embodiment of the invention shown in FIGS. 11-25, the locking plate is carried between the opposed pair of channels 46 on one or more of the plate sections, depending upon how many levels the plate system is intended to span. For a three level system as shown in FIG. 12, two locking plates would be required. In the two level plate system shown in FIGS. 11, 23 and 24, one locking plate 80 would be required and it would normally rest on either plate section 41 or plate section 42, depending upon how the plate system is oriented. After the plate sections are in position on the anterior surface of the cervical spine, the locking plate is slid across the hinged area 43 in the guide channels 46 and screws 81 are inserted through the openings 82 in the locking plate and openings 44 in the plate sections and into the vertebrae to secure all the components in place. Preferably, the locking plate is positioned at the caudal end of the plate system and pushed cranially to move it into locking position.

Figure 26:
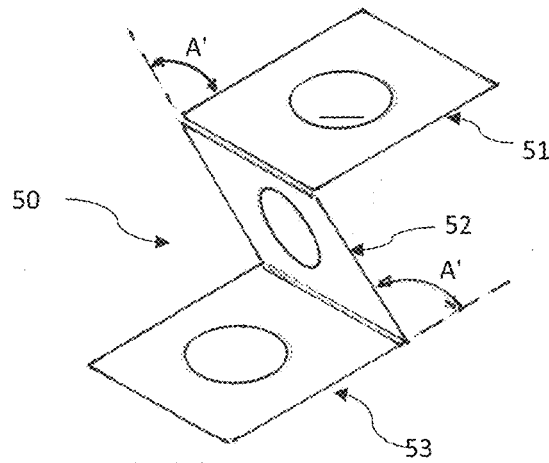
FIG. 26 is a schematic isometric view illustrating how three hinged together plate sections can be folded to shorten the overall length.
Figure 27:
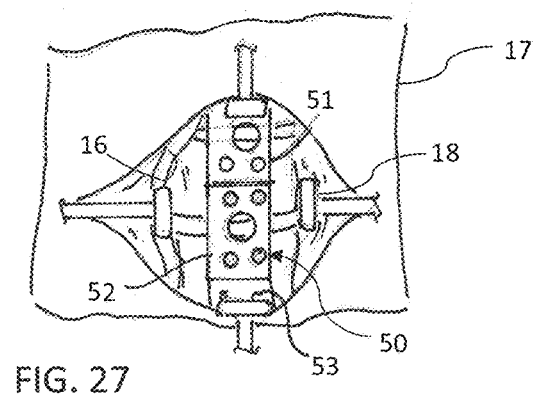
FIG. 27 is a fragmentary front view of a patient's neck, showing a transverse incision expanded with retractors and a single level plate section shown inn full lines in position on the cervical spine, with an additional plate shown in broken lines for a two level fusion.

FIG. 26 is a schematic illustration of how a three level system 50 can be folded to shorten its length for easier insertion into place, and FIG. 27 shows the system in position on the anterior surface of the cervical spine.

Figure 28:
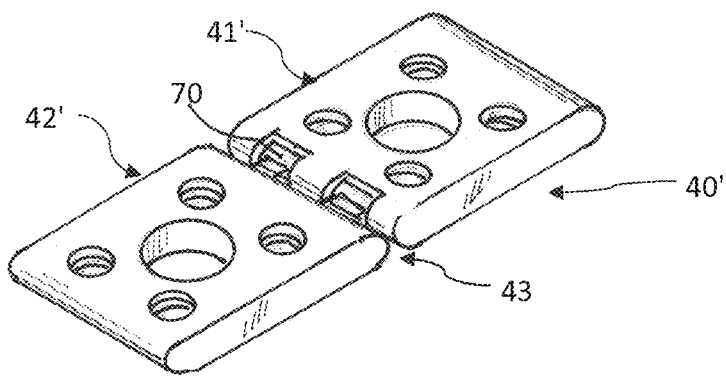
FIG. 28 is a top isometric view of an alternate form of the invention for two level fusion, wherein the guide channels are omitted.
Figure 30:
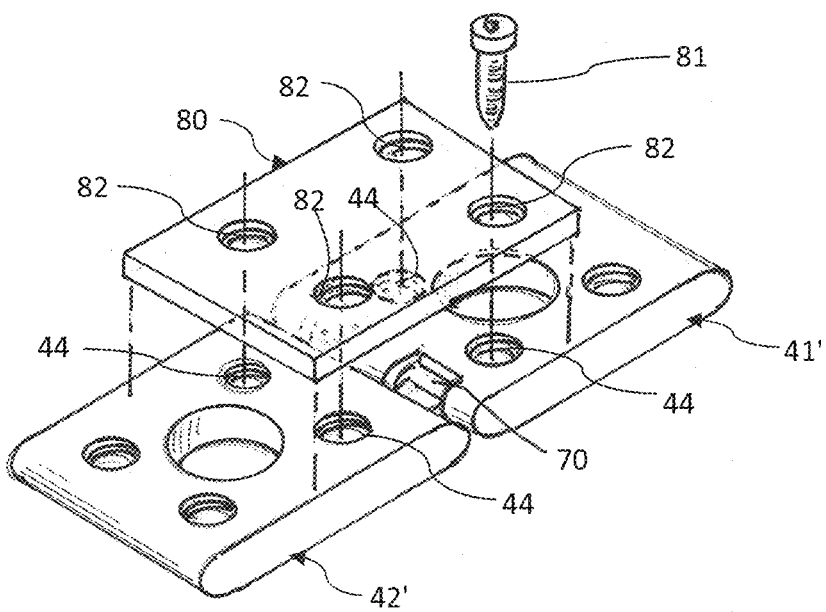
FIG. 30 is an exploded top isometric view of two hinged together plate sections in that form of the invention shown in FIG. 28, and a locking plate in position to be secured to the plate sections in spanning relationship to the hinged connection.
Figure 31:
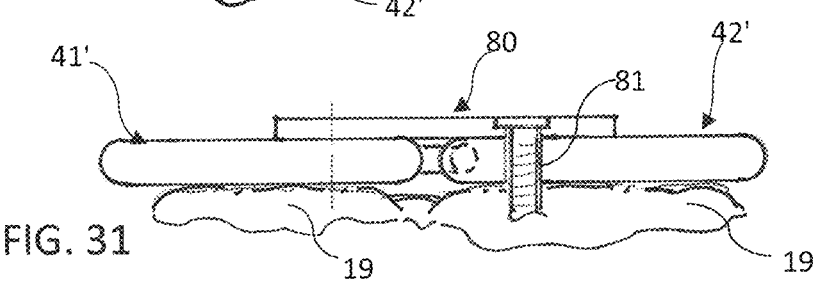
FIG. 31 is a fragmentary side view of two plate sections and a locking plate secured to the face of two vertebrae.

An alternate embodiment of the invention for two level fusion is indicated generally at 40' in FIG. 28. In this form of the invention, the guide channels 46 are omitted, and as shown in FIGS. 30 and 31, the locking plate 80 is placed on top of the plate sections 41', 42' in spanning relationship to the hinged area 43 after the plate sections are positioned on the anterior face of the cervical spine. Screws 81 are then inserted through the holes 82 in the locking plate and through the aligned holes 44 in the plate sections 41' and 42' and into the vertebral bodies 19. In all other respects this form of the invention is identical to that form shown in FIGS. 11-27.

Figure 29:
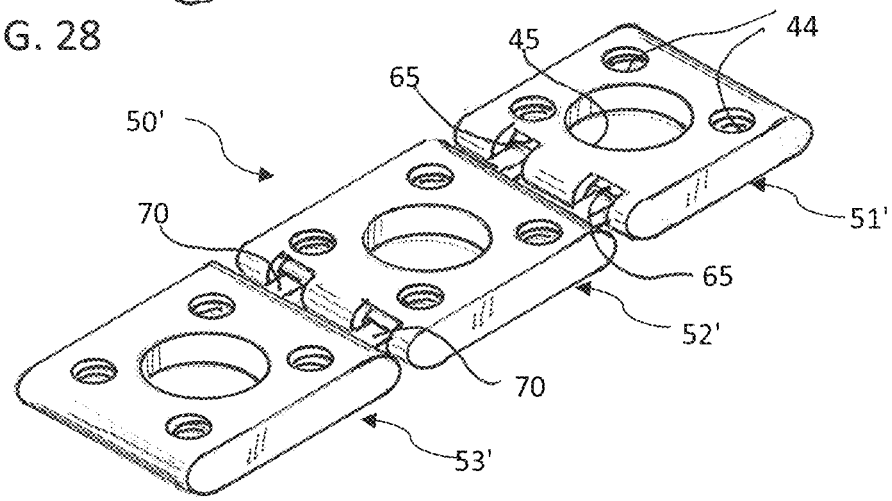
FIG. 29 is a top isometric view of the form of the invention shown in FIG. 28, but wherein an additional plate section is added for three level fusion.

FIG. 29 shows a three level variation 50' of the system 40' illustrated in FIGS. 28 and 30. This system is identical to that shown in FIGS. 28 and 30 except that an additional level is added. In this regard, it should be understood that additional levels could similarly be added, depending upon the requirements of the procedure being performed.

While particular embodiments of the invention have been illustrated and described in detail herein, it should be understood that various changes and modifications may be made to the invention without departing from the spirit and intent of the invention as defined by the scope of the appended claims.

What is claimed is:

1. A folding plate system for stabilizing adjacent vertebral bodies in a cervical spine, said plate system comprising:
   at least two plate sections hingedly connected together so as to form a hinged connection at and along adjacent ends such that the at least two plate sections are pivotable out of plane with one another at a common axis of rotation traversing overlapping portions of the adjacent ends;
   a visualization hole in each said plate section arranged and disposed for visualization of an underlying graft site; and
   a plurality of screw holes through each plate section for receiving screws inserted therethrough,
   wherein the visualization hole is enclosed around its periphery, and
   wherein the visualization hole includes a visualization hole size dimension greater than a size dimension of any of the plurality of screw holes.

2. The folding plate system as claimed in claim 1, wherein:
   said system includes a locking plate sized to extend across the hinged connection of two adjacent plate sections of the at least two plate sections and having a plurality of holes therethrough spaced to align with at least some of said plurality of screw holes in each said adjacent plate sections, whereby screws inserted through the screw holes in the locking plate and the adjacent plate sections are configured to lock the adjacent plate sections to resist pivoting movement of said plate sections.

3. The folding plate system as claimed in claim 2, wherein:
   a guide channel extends longitudinally along each of opposite side edges of each plate section, said locking plate being retained and guided at opposite side edges in said channels for sliding movement in said guide channels from an unlocked position on top of one of said plate sections to a locked position spanning the hinged connection of said two adjacent plate sections of the at least two plate sections.

4. The folding plate system as claimed in claim 3, wherein:
   said hinged connection comprises a pair of support arms extending from one end of a first plate section of said plate sections, a pivot pin supported by said support arms in spaced relation to said one end, and a bore extending transversely of one end of a second plate section of said plate sections, said pin being rotatably received in said bore to pivotally connect together said first plate section and second plate section.

5. The folding plate system as claimed in claim 4, wherein:
   a slot extends longitudinally in said one end of said second plate section in angularly offset relation below a plane of said second plate section, said slot opening into said bore and enabling said pivot pin to be inserted endwise into said bore, said slot terminating in spaced relation to an adjacent side edge of said second plate section, wherein an end of said slot forms a stop that limits how far the pivot pin can be inserted into said bore; and
   notches formed in said one end of said second plate section in spaced locations along said one end corresponding to locations of said support arms on said first plate section when said pivot pin of said first plate section is fully inserted into the bore of said second plate section, said notches extending transversely to said slot and terminating at their upper and lower extremities in upper and lower surfaces, respectively, of said second plate section to enable said plate sections to be pivoted up and down relative to one another.

6. The folding plate system as claimed in claim 5, wherein:
   the at least two plate sections comprise only said two adjacent plate sections that are hinged together to form a two-level system.

7. The folding plate system as claimed in claim 5, wherein:
   said plate sections and locking plate are made of titanium; and
   each plate section measures 2-3 mm in thickness, 6-10 mm in width, and 20-30 mm in length.

8. The folding plate system as claimed in claim 2, wherein:
   said system includes said at least two plate sections comprised of said two adjacent plate sections and an additional plate section to provide at least three plate sections that are hinged together to form a three-level system.

9. The folding plate system as claimed in claim 2, wherein:
   said hinged connection comprises a pair of support arms extending from one end of a first plate section of said plate sections, a pivot pin supported by said support arms in spaced relation to said one end, and a bore extending transversely of one end of a second plate section of said plate sections, said pin being rotatably received in said bore to pivotally connect together said first plate section and second plate section.

10. The folding plate system as claimed in claim 9, wherein:
a slot extends longitudinally in said one end of said second plate section in angularly offset relation below a plane of said second plate section, said slot opening into said bore and enabling said pivot pin to be inserted endwise into said bore, said slot terminating in spaced relation to an adjacent side edge of said second plate section, wherein an end of said slot forms a stop that limits how far the pivot pin can be inserted into said bore; and
notches formed in said one end of said second plate section in spaced locations along said one end corresponding to locations of said support arms on said first plate section when said pivot pin of said first plate section is fully inserted into the bore of said second plate section, said notches extending transversely to said slot and terminating at their upper and lower extremities in upper and lower surfaces, respectively, of said second plate section to enable said plate sections to be pivoted up and down relative to one another.

11. The folding plate system as claimed in claim 10, wherein:
the at least two plate sections comprise only said two adjacent plate sections that are hinged together to form a two-level system.

12. The folding plate system as claimed in claim 10, wherein:
said system includes said at least two plate sections comprised of said two adjacent plate sections and an additional plate section to provide at least three plate sections that are hinged together to form a three-level system.

13. The folding plate system as claimed in claim 12, wherein:
a guide channel extends longitudinally along each of opposite side edges of each plate section, said locking plate being retained and guided at opposite side edges in said channels for sliding movement in said guide channels from an unlocked position on top of one of said plate sections to a locked position spanning said adjacent ends and said hinged connection.

14. The folding plate system as claimed in claim 10, wherein:

said plate sections and locking plate are made of titanium; and
each plate section measures 2-3 mm in thickness, 6-10 mm in width, and 20-30 mm in length.

15. The folding plate system as claimed in claim 1, wherein the at least two plate sections hingedly connected together are arranged and disposed to hinge for pivoting movement through at least 90° in each of two directions relative to one another.

16. The folding plate system as claimed in claim 1, wherein at least one of the plate sections includes an end opposite the hingedly connected adjacent ends which is free of a hinge-forming structure.

17. The folding plate system as claimed in claim 1, wherein the plurality of screw holes through each plate section includes four screw holes through each plate section.

18. The folding plate system as claimed in claim 17, wherein the four screw holes are disposed adjacent to four corners of each plate section.

19. The folding plate system as claimed in claim 1, wherein the visualization hole is disposed at a center of each plate section.

20. A folding plate system for stabilizing adjacent vertebral bodies in a spine, said plate system comprising:
at least two plate sections hingedly connected together at a common axis of rotation traversing overlapping portions of the at least two plate sections, each plate section comprising:
a visualization hole arranged and disposed for visualization of an underlying graft site between the adjacent vertebral bodies; and
a plurality of screw holes for receiving screws inserted therethrough, the
plurality of screw holes disposed adjacent to four corners of the plate section,
wherein each of the plate sections includes an end opposite hingedly connected adjacent ends which includes a hinge-forming structure or is free of a hinge-forming structure,
wherein the visualization hole is enclosed around its periphery, and
wherein the visualization hole includes a visualization hole size dimension greater than a size dimension of any of the plurality of screw holes.

* * * * *